(12) United States Patent
Lombardo et al.

(10) Patent No.: US 7,189,238 B2
(45) Date of Patent: Mar. 13, 2007

(54) SOFT TISSUE ANCHOR

(75) Inventors: Giuseppe Lombardo, New Port Richey, FL (US); Robert K. Adikes, Jr., Largo, FL (US); Joseph Fucci, Tarpon Springs, FL (US)

(73) Assignee: Linvatec Corporation, Largo, FL (US)

( * ) Notice: Subject to any disclaimer, the term of this patent is extended or adjusted under 35 U.S.C. 154(b) by 475 days.

(21) Appl. No.: 10/666,644

(22) Filed: Sep. 18, 2003

(65) Prior Publication Data

US 2004/0059336 A1    Mar. 25, 2004

Related U.S. Application Data

(60) Provisional application No. 60/413,261, filed on Sep. 25, 2002.

(51) Int. Cl.
*A61B 17/58* (2006.01)
(52) U.S. Cl. ............................................. 606/72
(58) Field of Classification Search ............... 606/72, 606/73, 99, 104, 232, 233
See application file for complete search history.

(56) References Cited

U.S. PATENT DOCUMENTS

| 324,768 | A | * | 8/1885 | Hunt ........................... 411/358 |
| 4,468,200 | A | * | 8/1984 | Munch ........................ 433/174 |
| 5,013,316 | A | * | 5/1991 | Goble et al. .................. 606/72 |
| 5,601,558 | A | * | 2/1997 | Torrie et al. .................. 606/72 |
| 5,713,903 | A | * | 2/1998 | Sander et al. ................. 606/72 |
| 5,720,766 | A | * | 2/1998 | Zang et al. .................. 606/232 |
| 6,123,711 | A | * | 9/2000 | Winters ........................ 606/73 |
| 6,517,564 | B1 | * | 2/2003 | Grafton et al. ............. 606/213 |
| 6,648,893 | B2 | * | 11/2003 | Dudasik ....................... 606/73 |
| 2001/0051807 | A1 | * | 12/2001 | Grafton ........................ 606/72 |

\* cited by examiner

*Primary Examiner*—Eduardo C. Robert
*Assistant Examiner*—James L. Swiger
(74) *Attorney, Agent, or Firm*—Gene Warzecha

(57) ABSTRACT

A soft tissue anchor is provided for attaching soft tissue to bone. The anchor is useful generally throughout the body where soft tissue needs to be anchored to bone. It is particularly useful for reattaching separated tissues adjacent to an articular joint such as the hip, knee, or shoulder. For example it is well suited for reattaching labral tissue that has become separated from the glenoid rim adjacent a shoulder joint.

2 Claims, 1 Drawing Sheet

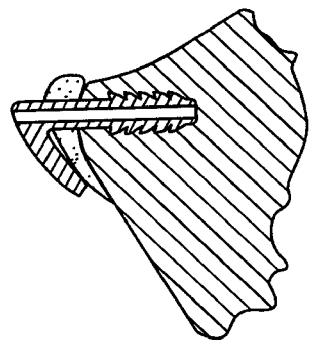
Fig. 1
(Prior Art)
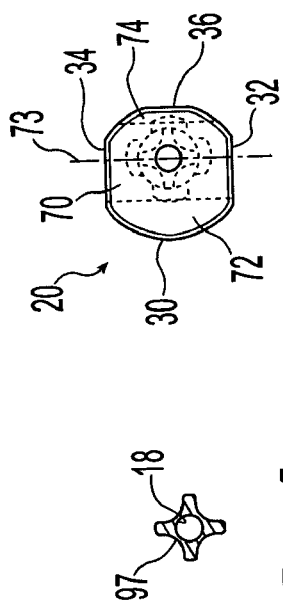
Fig. 3
Fig. 2
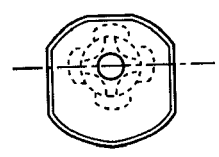
Fig. 5
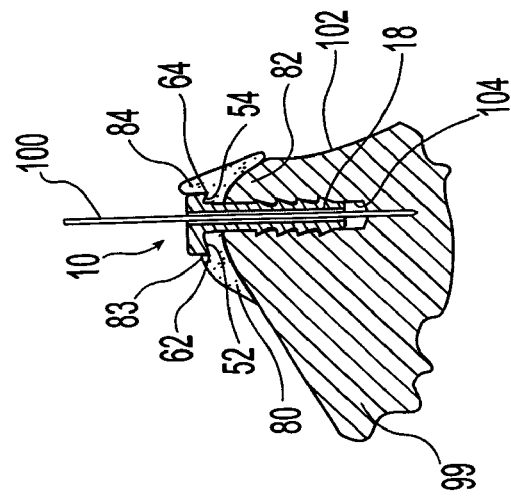
Fig. 4
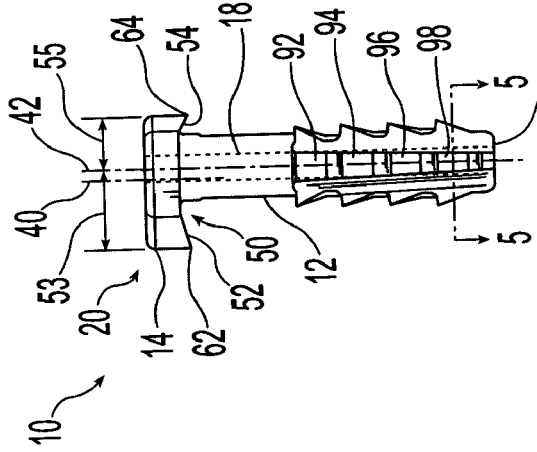
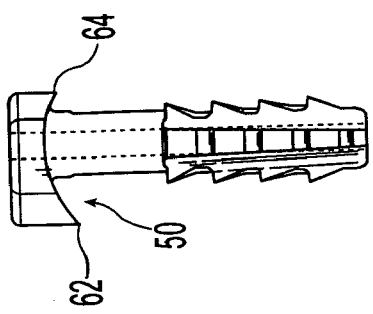
Fig. 7
Fig. 6

SOFT TISSUE ANCHOR

This application claims the benefit of U.S. Provisional Application No. 60/413,261, filed Sep. 25, 2002.

BACKGROUND

This invention relates to soft tissue anchors for securing soft tissue to bone. More particularly, this invention relates to a soft tissue anchor for securing labral tissue to the glenoid rim adjacent a human shoulder joint.

Throughout the human body, soft tissues connect to bone for various physiological reasons such as providing anchorage for muscles, connecting bones to one another, and providing protective capsules around joints, among others. For example, the human shoulder joint provides for articulation between the glenoid fossa of the scapula and the head of the humerus. The joint is surrounded by muscles and tendons that hold the joint together. These tissues connect to the glenoid rim of the scapula and form a fibrocartilage band around the glenoid fossa known as the glenoid labrum. In addition to being an anchorage for soft tissues around the shoulder joint, the glenoid labrum also deepens the glenoid fossa to form a more stable socket for the humeral head to fit within.

Various shoulder injuries, such as dislocations, falls, and throwing injuries, can result in the separation of the glenoid labrum from the glenoid rim. Different names have been attached to these separation injuries based on the location of the separation. For example, in a superior labral anterior posterior (SLAP) lesion, the labrum becomes separated near the top of the glenoid rim between the 11 o'clock and 1 o'clock positions. In a Bankart lesion, the labrum becomes separated between the anterior and inferior aspects of the glenoid rim between the 3 o'clock and 6 o'clock positions. Injuries such as these typically result in pain and instability in the shoulder joint. Treatment involves reattaching the labral tissue to the glenoid rim.

Soft tissue anchors for securing tissue to bone are known in the prior art, including anchors for connecting labral tissue to bone. Such devices are sometimes called tacks because they often have the appearance of a common tack. That is, the devices often have a shaft with a transverse head, the shaft having some projecting ribs, barbs or threads to enable the tack to be secured in the bone such as the glenoid rim. Most prior art tacks are suitable for reattaching many types of soft tissue and utilize symmetrical circular heads situated on an axially aligned shaft. However, recently a tack has been introduced with a non-symmetrical head particularly suitable for labral tissue as shown in FIG. 1. This device is generally "L"-shaped. The head extends only to one side of the shaft, away from the glenoid fossa, and extends at an angle of less than 90° from the shaft.

SUMMARY

The present invention provides a soft tissue anchor for attaching soft tissue to bone. It is useful generally throughout the body where soft tissue needs to be anchored to bone. It is particularly useful for reattaching separated tissues adjacent to an articular joint such as the hip, knee, or shoulder. For example it is well suited for reattaching labral tissue that has become separated from the glenoid rim adjacent a shoulder joint.

In one aspect of the invention, a soft tissue anchor for attaching soft tissue to a bone includes an elongated shaft and a transverse head at one end of the shaft. The transverse head extends in a first direction a first predetermined distance to a first point and in a second direction, generally opposed to the first direction, a second predetermined distance to a second point. The transverse head has a transverse bottom surface adjacent the shaft with a first projection extending distally from the first point and a second projection extending distally from the second point.

In another aspect of the invention, a soft tissue anchor for attaching soft tissue to a bone, includes an elongated shaft and a tissue engaging means affixed to the proximal end of the shaft. The shaft includes a plurality of radially outwardly extending barbs arranged in a plurality of linear, longitudinally extending rows. Each row contains a plurality of longitudinally spaced barbs and each barb has a width. The width of a barb in a row being greater than that of the immediately distally adjacent barb in that row such that upon insertion into bone, each barb cuts into bone undisturbed by the barbs distal to it.

In another aspect of the invention, a soft tissue anchor for attaching labral tissue to bone adjacent the glenoid fossa of a shoulder socket includes an elongated shaft and a tissue engaging means affixed to the proximal end of the shaft. The tissue engaging means includes means for holding the labral tissue adjacent the bone and means for expanding a portion of the labral tissue adjacent the glenoid fossa to create a raised tissue buttress adjacent the glenoid fossa.

In another aspect of the invention, a method of securing labral tissue to bone adjacent the glenoid fossa of a shoulder socket includes providing a soft tissue anchor; inserting the shaft through the labral tissue and into the bone; and pressing the soft tissue anchor against the labral tissue to hold the labral tissue adjacent the bone and to expand a portion of the labral tissue adjacent the glenoid fossa to create a raised tissue buttress adjacent the glenoid fossa.

BRIEF DESCRIPTION OF THE DRAWINGS

Various embodiments of the present invention will be discussed with reference to the appended drawings. These drawings depict only illustrative embodiments of the invention and are not to be considered limiting of its scope.

FIG. 1 shows a cross-sectional view of a prior art device in use to hold labral tissue adjacent a glenoid rim in a human shoulder.

FIG. 2 is a side elevation view of a soft tissue anchor constructed in accordance with the principles of this invention.

FIG. 3 is a top plan view of FIG. 2.

FIG. 4 is a cross-sectional view of the invention in use to hold labral tissue adjacent a glenoid rim in a human shoulder.

FIG. 5 is a cross section taken along line 5—5 of FIG. 2.

FIG. 6 is a side elevation of the soft tissue anchor of FIG. 2 showing an optional head configuration.

FIG. 7 is a top plan view of FIG. 6.

DESCRIPTION OF THE ILLUSTRATED EMBODIMENTS

FIGS. 2, 3, and 4 show an exemplary soft tissue anchor 10 for securing soft tissue to bone. The soft tissue anchor 10 may be used at various locations in the body. In the exemplary embodiments, the anchor is shown attaching labral tissue to the glenoid rim adjacent a human shoulder. These embodiments are by way of example and should not be construed to limit the tissue anchor 10 to labral tissue or to the shoulder joint. The anchor may also be used for example, to attach other soft tissues associated with the shoulder joint to bone as well as soft tissues associated with other areas of the body, including for example, the hip and knee joints.

The exemplary soft tissue anchor 10 of FIGS. 2, 3, and 4 includes an elongated shaft 12 having a shaft axis 42, a proximal end 14, and a distal end 16 for insertion into a bone. A low-profile transverse head 20 adjacent the proximal end 14 traps soft tissue adjacent the bone. An optional axially aligned lumen 18 permits the anchor to be inserted over a guide wire.

The transverse head 20 has a generally circular body 30 having flats 32, 34, 36 formed at circumferential locations around its rim. An opposing pair 32, 34 of flats facilitates orientation of the anchor relative to a driver and permits the driver to grip the sides of the head 20. A third flat 36 also facilitates orienting and gripping the head and minimizes intrusion of the head 20 laterally toward the humeral head of the shoulder joint. The head 20 has a centerline, or axis, 40 which is laterally offset from the shaft axis 42 so that the head 20 is asymmetrically attached to the shaft 12. The head 20 has a bottom surface 50 which extends generally transversely to the shaft axis 42 and has a first portion 52 which extends laterally away from the shaft axis 42 for a first predetermined distance 53 to overhang a first side of the shaft 12. The bottom surface 50 has a second portion 54 which is diametrically opposed to the first portion 52 and extends laterally away from the shaft axis 42 for a second predetermined distance 55 to overhang a second, opposite, side of the shaft 12. In the embodiment shown, the second predetermined distance 55 is less than the first predetermined distance 53. Each of the first 52 and second 54 portions has a distally extending first 62 and second 64 edge, respectively, which projects distally from the bottom surface 50 to grip soft tissue. The first predetermined distance 53 is sufficiently long for the bottom surface 50, first portion 52, and edge 62 to hold the tissue securely and prevent it from sliding over the head 20. In the preferred embodiment, first portion 52 extends from shaft axis 42 approximately 2–5 mm beyond the surface of the shaft. The second predetermined distance 55 is sufficiently long for the bottom surface 50, second portion 54, and edge 64 to grip the tissue while not being so long as to intrude into the joint space. In the preferred embodiment, the second portion 54 extends 0.25–2 mm beyond the surface of the shaft. The relative dimensions of anchor 10 are approximately to scale.

The bottom surface 50 may be planar and perpendicular to the shaft axis 42 in all areas except at the perimeter, as at transitions to edges 62 and 64. However, the bottom surface 50 may advantageously be shaped to fit the curvature of the underlying bone to improve the clamping action of the head 20 on the soft tissue. For example, in the embodiment of FIGS. 2 and 3, the bottom surface 50 is flat and perpendicular in a central area 70 and flat and ramped in peripheral areas 72 and 74 to form a concavity about an axis 73 parallel to the edges 62 and 64. These ramped areas 72 and 74 may approximate the curvature of an underlying bone such as a glenoid rim. Alternatively, the bottom surface 50 may be smoothly curved between the edges 62 and 64 about the axis 73 to more closely conform to a smoothly curved underlying bone, as shown in FIGS. 6 and 7.

The shaft 12 includes barbs 92, 94, 96, 98 arranged in four linear rows spaced circumferentially about the shaft axis 42 on the shaft surface. A radius 97 connects each pair of adjacent rows of barbs so that the barbed shaft 12 is generally in the form of a four-pointed star as shown in FIG. 5. The barbs have varying predetermined arcuate widths, best seen in FIGS. 2 and 5, such that each barb in a given row has an arcuate width that is greater than the next adjacent proximal barb. That is, barb 92 is wider than barb 94 which is wider than barb 96 which is wider than barb 98. All barbs in a common annular row may have the same arcuate width. This feature enables following barbs to always engage virgin bone as anchor 10 is pushed into a bone tunnel, thus enhancing fixation strength.

The soft tissue anchor 10 may be made of any suitable biocompatible material. For example, it may be made of resorbable polymers, non-resorbable polymers, metals, ceramics, and other suitable materials. Some examples of these types of materials include poly lactic acid, poly (L-lactic acid), polyester, polytetrafluroethylene, polyethylene, polyetheretherketone, stainless steel, titanium, nitinol, tantalum, zirconia ceramic, alumina ceramic, and other suitable materials. The soft tissue anchor 10 may be formed by molding, machining, sintering, or other suitable process. For example, the soft tissue anchor 10 may be advantageously injection molded from poly (L-lactic acid) to produce a strong, radiolucent, implant that is metabolized by the body after the soft tissue has had sufficient time to heal.

FIG. 4 shows the exemplary use of the soft tissue anchor 10 on the glenoid 99 to reattach labral tissue 80 that has become separated from the glenoid rim 82 adjacent the glenoid fossa 102 of the shoulder joint. In such a procedure, the surgeon gains access to the site of the tissue separation such as with a cannula inserted through the tissues surrounding the shoulder. The labral tissue 80 is repositioned in the correct anatomic position and pinned in place with a guide wire 100. A drill is inserted over the guide wire and drilled through the labral tissue 80 and into the bone of the glenoid rim 82 to form a pilot hole 104. The drill is then removed and the soft tissue anchor 10 is positioned with the guide wire 100 in the lumen 18. The soft tissue anchor 10 is passed along the guide wire 100 and into the pilot hole 104. The soft tissue anchor 10 is impacted so that the bottom surface 50 of the head 20 presses the labral tissue 80 against the glenoid rim 82. The edges 62 and 64 grip the labral tissue 80 and press down into the tissue 80 causing a pin cushion effect such that the tissue bulges up around the head 20 to create soft tissue buttresses 83 and 84. The buttresses 83 and 84 shield the head 20 to prevent it from impinging on the humeral head and deepen the shoulder socket to help stabilize the joint. The second edge 64 grips the labral tissue 80 adjacent the glenoid fossa 102 so that medially directed pressure against the tissue 80, for example by the humeral head, will not push the tissue up the shaft 12 and over the head 20. Instead, such medially directed pressure will cause the tissue 80 to bulge up even further, enhancing the buttress 84 and further shielding the head 20 and deepening the shoulder socket.

It will be understood by those skilled in the art that numerous improvements and modifications may be made to the preferred embodiment of the invention disclosed herein without departing from the spirit and scope thereof.

What is claimed is:

1. A soft tissue anchor for attaching soft tissue to a bone, the soft tissue anchor comprising:
    an elongated shaft having an axis, a proximal end, and a distal end;
    a bone engaging means affixed to the shaft for securing the distal end of the shaft in the bone; and
    a transverse head engageable with the soft tissue to be attached to the bone, the transverse head extending in a first direction to a first point situated a first predetermined distance outwardly from the axis and extending in a second direction, generally opposed to the first direction, to a second point situated a second predetermined distance outwardly from the axis, the second predetermined distance being less than the first predetermined distance, the transverse head having a width equal to or greater than that of the proximal end of the shaft and the transverse head having a transverse bottom surface adjacent the shaft, a first projection extending a third predetermined distance distally from the first point, a second projection extending a fourth predetermined distance distally from the second point wherein the transverse head further comprises a circular member having a centerline offset a perdetermined distance laterally from the axis of the shaft, the circular member including a first flattened rim adjacent the second point.

2. A soft tissue anchor according to claim 1 further comprising a pair of diametrically opposed flattened rim portions orthogonally situated relative to the first flattened rim.

* * * * *